United States Patent [19]

Goupil

[11] Patent Number: 5,962,512
[45] Date of Patent: Oct. 5, 1999

[54] OIL CONTAINING 5-METHOXYPSORALEN AT A CONCENTRATION OF 60-100 PPM, AND ITS USE IN TREATMENT OF PSORIASIS

[76] Inventor: Jean Jacques Goupil, 23 Quai Le Gallo, Boulogne, France, 92100

[21] Appl. No.: 08/525,952

[22] Filed: Sep. 8, 1995

Related U.S. Application Data

[63] Continuation of application No. 08/126,581, Aug. 25, 1993, abandoned.

[30] Foreign Application Priority Data

Sep. 3, 1992 [FR] France .................................. 92.10523

[51] Int. Cl.$^6$ ...................................................... A61K 31/35
[52] U.S. Cl. .............................................................. 514/455
[58] Field of Search .............................................. 514/455

[56] References Cited

U.S. PATENT DOCUMENTS

| | | | |
|---|---|---|---|
| 4,130,568 | 12/1978 | Confolone | 260/343.21 |
| 4,147,703 | 4/1979 | Liebman et al. | 260/343.21 |
| 4,217,445 | 8/1980 | Nikolaiski | 563/4 |
| 4,429,138 | 1/1984 | Goupil | 549/282 |
| 4,699,781 | 10/1987 | Goupil | 424/59 |
| 4,868,311 | 9/1989 | Saffran et al. | 548/303 |
| 4,970,230 | 11/1990 | Goupil | 514/455 |
| 5,200,425 | 4/1993 | Goupil | 514/455 |

FOREIGN PATENT DOCUMENTS

| | | |
|---|---|---|
| 156 287 | 3/1985 | European Pat. Off. . |
| 538 053 | 4/1993 | European Pat. Off. . |
| 2409751 | 6/1979 | France . |
| 2003470 | 3/1979 | United Kingdom . |
| 93/25872 | 12/1993 | WIPO . |

OTHER PUBLICATIONS

Young et al., *J. Photochem. Photobiol.*, B, 7(2–4), pp. 231–250. 1990.
Sakuntabhai et al., Br. J. Dermatol. 128/3, (296–300) 1993.
Tiefenauer et al., *J. Steroid Biochem.*, vol. 32, No. 2, pp. 251–257 (1989) & Co., Inc. Rahway, N.J., (1976).

J. De Boever et al., *Analytica Chimaca Acta*, vol. 170, pp. 117–123 (1985).

Brinkley, Michael (1992), *Bioconjugate Chemistry*, vol. 3, pp. 2–13.

Luppa, P., et al. (1994), *Bioconjugate Chemistry*, vol. 5, pp. 167–171.

Gosling, James P. (1990), *Clin. Chem.* 36:(8), pp. 1408–1427.

Kabakoff, David S., "Chemical Aspects of Enzyme Immunoassay", Chptr. 4, (1980).

64:4125f, *Chemical Abstracts* (1966).

Stedman's Medical Dictionary, 21st ed., p. 430 (1966).

The Merck Index, 9th Ed., p. 433, Merck & Co., Inc. Rahway, N.J., (1976).

Handbook of Non Prescriptioned Drugs, 5:331–333 (1977).

Parrish, John A. et al., *The New England Journal of Medicine*, 291:(23), 1204–1211 (1974).

Grupper, C., et al., *Dermatologica*, 162:404,413 (1981).

Honigsmann, Herbert et al., *British Journal of Dermatology* 101: 369–378 (1979).

Berretti, B. et al., *Le Praticien n° 423*, pp. 47–51, Mar. 16, 1982.

Epstein, Ervin, "Controversies in Dermatology", W.B. Saunders Co. (1984).

*Primary Examiner*—Phyllis G. Spivack
*Attorney, Agent, or Firm*—Hughes Hubbard & Reed LLP; Ronald Abramson; Peter A. Sullivan

[57] ABSTRACT

The invention relates to topically applied pharmaceutical compositions containing 5-methoxypsoralen in a concentration of 60 ppm to 100 ppm, and more particularly 65 to 95 ppm, and preferably 75 ppm, in a pharmaceutically acceptable oleaginous formula, as well as the use of these compositions in the treatment of psoriasis.

11 Claims, No Drawings

OIL CONTAINING 5-METHOXYPSORALEN AT A CONCENTRATION OF 60-100 PPM, AND ITS USE IN TREATMENT OF PSORIASIS

This is a continuation of application Ser. No. 08/126,581, filed Aug. 25, 1993, now abandoned.

The present invention has as its object pharmaceutical compositions intended for the topical treatment of psoriasis and other dermatoses, comprising 5-methoxypsoralen (or 5-MOP) in a concentration of 60 ppm to 100 ppm, in a pharmaceutically acceptable oleaginous formulation.

BACKGROUND OF THE INVENTION

Psoriasis is a skin disease characterized by a hyperproliferation of keratinocytes and a disorder in their differentiation.

An inflammation of the dermis also arises, with vascular and immunological changes involving an activation of T lymphocytes.

This hereditary disorder, benign in the great majority of cases, manifests itself in more or less extensive erythematosquamous plaques on the cutaneous integument, causing sometimes great suffering for the patient and for those around the patient.

Though often localized at the elbows and forearms, on the knees and legs, and in the lumbar and gluteal region, the lesions can extend to the rest of the body.

Sometimes, on account of its great extent, amounting to a *psoriasis universalis* or even an erythrodermic psoriasis, due to its particular pustular form or to its association with arthritis, psoriasis amounts to a very grave and crippling disease that may place a patient's vital or functional prognosis at risk.

The treatment of psoriasis by the oral administration of 5-methoxypsoralen in doses between 1 mg and 1.2 mg per kilogram of body weight, by a session of PUVA therapy, and further ultraviolet irradiation, has been covered by French Patent 2,406,444.

On account of the difficulties involved in prolonged general PUVA treatments it is particularly important to be able to have a local treatment on a body area exposed to reduced ultraviolet radiation.

The present invention has precisely the purpose of providing a composition making it possible to avoid certain problems involved in oral treatment, and to proceed in particular with a topical treatment of psoriasis of limited extent or of stubborn plaques, which have subsisted after oral treatment.

The present invention has as its subject matter a pharmaceutical composition intended for topical application, characterized in that it comprises 5-methoxypsoralen (5-MOP) in a concentration of 60 ppm to 100 ppm, and more particularly of 65 ppm to 95 ppm, in a pharmacologically acceptable oleaginous formula.

Compositions particularly preferred in the scope of the present invention include 5-MOP in a concentration of the order of 75 ppm.

Natural essences of citrus, such as the essence of natural bergamot, which contains 5-methoxypsoralen, are generally used.

The pharmaceutical compositions of the invention also include one or more ultraviolet B ray filters, selected from among ethyl-hexyl paramethoxycinnamate, trimethylbenzylidene heptanone, etc.

The compositions of the invention are presented in an oily excipient or in the form of continuous-phase lipidic emulsions.

By way of example, the following composition can be given, which is in an oleaginous form and comprises:

| | |
|---|---|
| Peanut oil | 68.970% |
| Isopropyl myristate | 25.000% |
| Ethyl-2-hexyl-p-methoxycinnamate | 2.000% |
| 1,7,7-trimethyl-3-(methyl-4-benzyl-idene)-bicyclo-(2,2,1)-2-heptanone | 1.000% |
| Natural essence of bergamot, amount sufficient for 75 ppm of 5-MOP | |
| Synthetic citrus essence, sufficent to make 3% | 3.000% |
| Butylhydroxyanisole | 0.020% |
| Butylhydroxytoluene | 0.010% |

The invention more particularly contemplates the use of natural citrus essences giving to the finished product a 5-MOP concentration between 60 and 100 ppm, particularly between 65 and 95 ppm, and more particularly a concentration of 75 ppm, in an oleaginous excipient, to obtain a medicament useful in the topical treatment of psoriasis and of a certain number of dermatoses such as parapsoriasis, vitiligo, and atopic eczema.

The compositions according to the invention are applied to the areas of the skin to be treated about 30 minutes to one hour before these areas are irradiated with ultraviolet light. The initial dose of UVA varies from 1 to 4 joules per $cm^2$ according to the skin phototypes, the final dose (for the last treatment sessions) not exceeding 6 joules/$cm^2$. The treatment is continued generally at the rate of 3 sessions per week for 4 to 6 weeks.

Thirty patients, of ages 15 years and up, all affected by localized psoriasis, in plaques, for 6 months without remission, were treated thus with the composition of the invention containing 75 ppm of 5-MOP described above, at the rate of three sessions per week. The composition of the invention was applied about 30 minutes before UVA irradiation in a Dixwell booth. The UVA dose was increased by 0.5 joules every two sessions until the patient was cleared.

It was found that, remarkably, the treatment with the composition according to the invention, given at 75 ppm of 5-MOP, produces no side effect, no itching, no secondary irritation after the application of the product, i.e. perfect tolerance in 25 patients out of 30. In 5 patients a persistent erythema appeared during the first sessions. As regards the results, of the 30 cases treated, 25 psoriases were cleared up completely or almost completely, 4 showed good improvement, and one only light improvement.

With the compositions of the invention, administered at 60 ppm of 5-MOP, the result of complete clearing was obtained by treatments extending over 4 to 10 weeks.

The measure of the improvements obtained was made by means of the severity index (which takes into account the erythema, the scaling and the thickness of the plaque) which permits assessing the gravity of the psoriasis and an understanding of the clinical aspect of an improvement.

The topical treatment described above can be used to supplement oral PUVA treatment in which a dose of 5-MOP on the order of 1 mg/kg is administered to the patient about two hours before irradiation. These combined treatments are particularly recommended for psoriasis extending over more than 40% of the body surface, and for removing refractory plaques.

It is interesting to note that the association of topic treatments with oral treatments permits reducing the number of sessions of PUVA therapy to a considerable extent, as much as 25%, which is obviously to the benefit of the patient and of public health.

I claim:

1. A method of treating dermatoses, said method comprising topically administering a composition comprising natural citrus essences and 5-methoxypsoralen (5-MOP) in an amount of between about 75 ppm and about 100 ppm.

2. A method as defined in claim 1, wherein said 5-methoxvpsoralen (5-MOP) concentration ranges between about 75 ppm to about 95 ppm.

3. A method as defined in claim 2, wherein said 5-methoxypsoralen (5-MOP) concentration is about 75 ppm.

4. A method as defined in claim 2, wherein said dermatoses are selected from the group consisting of psoriasis, parapsoriasis, vitiligo, and atopic eczema.

5. A method of treating dermatoses, said method comprising topically administering a composition consisting essentially of natural citrus essences and 5-methoxypsoralen (5-MOP) in an amount of between about 75 ppm and 100 ppm.

6. The method as defined in claim 5, wherein said concentration of 5-methoxypsoralen (5-MOP) is about 75 ppm.

7. The method as defined in claim 5, wherein said dermatoses are selected from the group consisting of psoriasis, parapsoriasis, vililigo and atopic eczema.

8. A method of treating dermatoses comprising the step of topically administering a pharmaceutical composition consisting essentially of 5-methoxypsoralen (5-MOP) as an active substance in a concentration of about 75 ppm to about 100 ppm in a pharmaceutically acceptable oleaginous formula.

9. A pharmaceutical composition for topical administration consisting essentially of 5-methoxypsoralen (5-MOP) as an active substance in a concentration of about 75 ppm to about 100 ppm in a pharmaceutically acceptable oleaginous formula.

10. Pharmaceutical composition defined in claim 9, characterized in that it is in an oleaginous form and contains:

| | |
|---|---|
| Peanut oil | 68.970% |
| Isopropyl myristate | 25.000% |
| Ethyl-2-hexyl-p-methoxycinnamate | 2.000% |
| 1,7,7-trimethyl-3-(methyl-4-benzyl-idene)-bicyclo-(2,2,1)-2-heptanone | 1.000% |
| Natural essence of bergamot q.s.p. amount sufficient to make 75 ppm of 5-MOP | |
| Synthetic citrus essence q.s.p. 3% | 3.000% |
| Butylhydroxyanisole | 0.020% |
| Butylhydroxytoluene | 0.010% |

11. A pharmaceutical composition for topical administration consisting essentially of 5-methoxypsoralen (5-MOP) as an active substance in a concentration of about 75 ppm to about 100 ppm, and an ultra violet B ray filter in a pharmaceutically acceptable oleaginous formula.

* * * * *